United States Patent [19]

Greene et al.

[11] Patent Number: 5,137,804

[45] Date of Patent: Aug. 11, 1992

[54] ASSAY DEVICE AND IMMUNOASSAY

[75] Inventors: Richard A. Greene, Westford, Mass.; Patricia A. Kasila, Windham, N.H.

[73] Assignee: E. I. Du Pont de Nemours and Company, Wilmington, Del.

[21] Appl. No.: 192,087

[22] Filed: May 10, 1988

[51] Int. Cl.[5] .................. C12Q 1/70; G01N 33/53
[52] U.S. Cl. ............................ 435/5; 435/6;
435/7.36; 435/7.4; 435/7.5; 435/7.92; 435/21;
435/28; 435/962; 435/970; 436/169; 436/528;
436/530; 436/535; 436/807; 436/810; 422/56;
422/60; 422/101
[58] Field of Search ............... 435/5, 6, 7, 21, 28,
435/805, 810, 7.1, 7.9, 7.5, 7.36, 7.32, 7.92, 7.94,
962, 7.4, 13, 969, 970; 436/512, 518, 528-535,
169, 170, 807, 825, 810; 422/55-58, 60, 101

[56] References Cited

U.S. PATENT DOCUMENTS

| 31,006 | 8/1982 | Schuurs et al. | 435/7 |
|---|---|---|---|
| 2,785,057 | 3/1957 | Schwab et al. | 422/58 |
| 3,011,874 | 12/1961 | Deutsch | 422/56 X |
| 3,232,710 | 2/1966 | Rieckmann et al. | 435/805 X |
| 3,249,513 | 5/1966 | Babson | 435/12 X |
| 3,341,427 | 9/1967 | Evans et al. | 435/34 X |
| 3,420,205 | 1/1969 | Morison | 422/59 X |
| 3,482,943 | 12/1969 | Csizmas et al. | 422/56 |
| 3,511,608 | 5/1970 | Anderson et al. | 435/805 X |
| 3,620,677 | 11/1971 | Morison | 422/59 X |
| 3,663,374 | 5/1972 | Moyer et al. | 195/103.5 R |
| 3,715,192 | 2/1973 | Wenz et al. | 422/56 |
| 3,723,064 | 3/1973 | Liotta | 435/7 X |
| 3,783,105 | 1/1974 | Moyer et al. | 195/127 |
| 3,791,933 | 2/1974 | Moyer et al. | 195/127 |
| 3,802,842 | 4/1974 | Lange et al. | 435/805 X |
| 3,888,629 | 6/1975 | Bagshawe | 435/7 X |
| 3,896,217 | 7/1975 | Johnson | 424/1 |
| 3,901,657 | 8/1975 | Lightfoot | 422/55 |
| 4,087,248 | 5/1978 | Miles | 424/1 X |
| 4,092,115 | 5/1978 | Rupe et al. | 436/169 X |
| 4,098,876 | 4/1978 | Piasio et al. | 424/1 |
| 4,200,690 | 4/1980 | Root et al. | 435/7 |
| 4,201,763 | 5/1980 | Monthony et al. | 424/8 |
| 4,235,601 | 11/1980 | Deutsch et al. | 23/230 R |
| 4,244,940 | 1/1981 | Jeong et al. | 424/1 |
| 4,246,339 | 1/1981 | Cole et al. | 435/7 |
| 4,258,001 | 3/1981 | Pierce et al. | 422/56 |
| 4,277,560 | 7/1981 | Gray et al. | 435/7 |
| 4,361,537 | 11/1982 | Deutsch et al. | 422/56 |
| 4,366,241 | 12/1982 | Tom et al. | 435/7 |
| 4,391,904 | 7/1983 | Litman et al. | 435/7 |
| 4,407,943 | 10/1983 | Cole et al. | 435/7 |
| 4,472,498 | 9/1984 | Masuda et al. | 435/7 |
| 4,549,655 | 10/1985 | Forsythe et al. | 206/569 |
| 4,581,331 | 4/1986 | Richards et al. | 435/5 |
| 4,632,461 | 11/1986 | Hossum et al. | 422/101 X |
| 4,632,901 | 12/1986 | Valkirs et al. | 435/5 |
| 4,652,533 | 3/1987 | Jolley | 436/518 |
| 4,748,115 | 5/1988 | Steaffen | 435/21 |
| 4,818,677 | 4/1989 | Hay-Kaufman et al. | 435/4 |
| 4,828,980 | 5/1989 | Snyder et al. | 435/7 |
| 4,849,505 | 7/1989 | Stavrianopoulos | 435/5 |
| 5,006,464 | 4/1991 | Chu et al. | 435/7.1 |

FOREIGN PATENT DOCUMENTS

| 0200381 | 11/1986 | European Pat. Off. | 436/533 |
|---|---|---|---|
| 239222 | 9/1987 | European Pat. Off. | 422/60 X |
| 1348938 | 3/1974 | United Kingdom | 435/7 |
| 1401297 | 7/1975 | United Kingdom | 435/7 |
| 1401298 | 7/1975 | United Kingdom | 435/7 |
| 2001172A | 1/1979 | United Kingdom | 435/7 |
| 2008767A | 6/1979 | United Kingdom | 436/525 X |
| 2018986A | 10/1979 | United Kingdom | 435/18 X |
| 1564578 | 4/1980 | United Kingdom | 436/500 X |

OTHER PUBLICATIONS

Zitex Product Literature, C100 (1985).
Zitex Product Literature, FTL-11D-5M987SA (1987).
Zitex Product Literature, G100 Series.
Grant & Hackh's Chemical Dictionary, p. 241, 5th Edition (1987).
Stenesh Dictionary of Biochemistry, pp. 147 & 154, John Wiley & Sons (1975).
Greene et al., 1988 ASM Annual Mtg., May 8-13, 1988, Miami Bch., Fla. (Abstract).
Millipore Immunozyme Toxoplasma Antibody Test, No. PD847 (1979).
Litman et al., Clin. Chem., pp. 1598-1603, vol. 29, No. 9 (1983).

*Primary Examiner*—Esther L. Kepplinger
*Assistant Examiner*—Carol A. Spiegel

[57] ABSTRACT

This invention relates to an improved assay device and assay for detecting or quantitating the presence or absence of a substance in a sample. The device has multiple layers comprising a permeable layer (a) having a capture reagent attached to less than the entire membrane, a selectively permeable layer (b) which does not allow assay reagents to pass through (b) and an absorbent layer (c). Layer (b) is in communication with layers (a) and (c). Layer (b) has at least one hole extending therethrough and the hole or holes are directly below the capture reagent in layer (a). The area of the hole or the combined area of the holes is less than the area covered by the capture reagent. This invention also relates to a method of reducing background color development in an absorbent layer of an assay device.

25 Claims, 1 Drawing Sheet

ASSAY DEVICE AND IMMUNOASSAY

FIELD OF THE INVENTION

This invention relates to a membrane-based assay device and immunoassay and, more specifically, to a multiple-membrane based device and immunoassay including a selectively permeable membrane.

BACKGROUND

Several assay devices are currently marketed. Typically, sandwich immunoassays are performed on these devices using a capture antibody immobilized on a filter or membrane, either directly or indirectly through trapping of antibody-coated latex particles. The specimen or an extract of it is applied to a device containing the filter or membrane with immobilized capture antibody. These commercial devices utilize capillary action to cause the sample and reagents to flow through the filter or membrane into an absorbent material lying beneath it. A sandwich is eventually formed in which one member is labeled with an appropriate signal-generating substituent, e.g. an enzyme label. Addition of substrate will detect the enzyme label by reacting with the enzyme to produce a colored reaction product. Since the enzyme is attached to a member of a sandwich whose existence requires the presence of the antigen, the colored reaction indicates the presence of the antigen as well. Several disadvantages plague these devices, one of which is the poor sensitivity of the assays. For example, specimens containing as many as $10^{11}$ target molecules/mL are usually needed in order for these assays to measure analytes such as human chorionic gonadotropin. One reason for the poor sensitivity is the difficulty of controlling the rate of capillary flow in the assay device. Reagents are removed from the reaction zone by capillary flow before the reactions are complete. More time for antigen-antibody interaction and other steps in building the sandwich or assaying the enzyme would improve the kinetics and allow the detection of smaller amounts of analyte. Another problem plaguing some assay devices having multilayer structures is the development of background color in an absorbent layer which interferes with discriminating between weak positive results and negative results.

One approach to resolve the difficulty in controlling the capillary flow rate is set forth in U.S. Pat. No. 4,366,241, issued to Tom et al., on Dec. 28, 1982, which discloses a method and apparatus for performing sandwich immunoassays. The apparatus is described as comprising an immunosorbing layer to which a member of an immunological pair is attached, a liquid absorbing member and a bibulous liquid flow-resistant disk. The bibulous liquid flow-resistant disk retards entry of liquid to the absorbent layer so that a uniform flow rate is achieved for liquid flowing through the immunosorbing member. Flow is not restricted to the particular area where the member of an immunological pair is immobilized on the immunosorbing member.

Tom et al. further discloses preventing signal production in a first layer of a multilayer immunosorbing zone by adding an enzyme to an intermediate layer to prevent the transfer of compounds from the detection layer. The example provided in column 13 states that the detector enzyme is present in a first layer and in a third layer. The system is designed so that detection occurs in the third layer. The substrate is not added to the first layer; instead it is generated in situ in the third layer. Another enzyme is present in the layer between the first layer and third layer which prevents any substrate from migrating from the third layer to the first layer so that detection occurs only in the third layer. There is no teaching of reducing background color in an absorbent layer by treating the absorbent layer with an enzyme inhibitor which acts directly on the enzyme.

Both U.S. Pat. No. 4,632,901, issued to Valkirs et al. on Dec. 30, 1986, and U.S. Pat. No. 4,092,115, issued to Rupe et al. on May 30, 1978, relate to devices having a structure located above a filter or membrane which permits sample flow onto a permeable member to which a reagent may be attached.

U.S. Pat. No. 4,623,461, issued to Hossum et al. on Nov. 18, 1986, discloses a transverse flow diagnostic device which can be used to perform a variety of immunoassays. The device is structured so that all fluids and reactants flow outwardly through the filter means from the point of application on to a localized portion of the top surface of the filter to peripheral portions of the filter. The absorbent means located in the peripheral portion of the device exercises a transverse capillary action to pull liquid outwardly from the point of application in the filter plane.

U.S. Pat. No. 4,407,943, issued to Cole et al. on Oct. 4, 1983, discloses immobilization of an antigen or antibody on zein-coated internal and external surfaces of a microporous membrane whose surfaces are rendered immunochemically reactive. It is disclosed that structures having large ratios of surface exposed to the volume of fluid flowing through the membrane are used in an attempt to increase the probability of reactive contact with the surface and reduce reaction time. The incubation time is governed by a technique whereby fluid is applied dropwise to the upper surface of the membrane so that the rate of flow of fluid is governed only by the hydrostatic pressure exerted by the drop as it rests on top of the membrane. An absorbent layer is not employed to exert a capillary action to pull the reagents therethrough.

U.S. Pat. No. 4,246,339, issued to Cole et al. on Jan. 20, 1981, discloses a multilayered device for testing liquid samples for the presence of predetermined components. The test device comprises telescoping top and base members which define a liquid reservoir, the top member has one or more test wells which open to the periphery of a microporous membrane. The microporous membrane has a co-reactant immobilized to its internal and external surfaces, which co-reactant is capable of reacting with the analyte. When a resilient means is depressed, the membrane contacts an absorbent member capable, by blotting or capillary action, of absorbing all the liquid passed through the test wells. Unless there is an absorbent layer and a means for bringing it into contact with the lower surface of the membranes, liquid will not pass through the membranes. When the device is not depressed no liquid will pass through the microporous membrane. The absorbent layer comprises a surface layer which is substantially non-wettable, i.e., for normal aqueous solutions it is comparable to the inner lining of diapers, and a substantially wettable layer.

U.S. Pat. No. 3,888,629, issued to Bagshawe on Jun. 10, 1975, discloses a reaction cell, suitable for use in radioimmunoassay, comprising a container having a matrix pad and a support for the matrix pad allowing liquid to flow therethrough. The matrix comprises a porous absorptive material which can bind analyte. The desired chemical reaction can occur within the matrix. Rail filtration is induced by employing a porous cellular material substantially in contact with the matrix.

U.S. Pat. No. 3,723,064, issued to Liotta on Mar. 27, 1973, discloses a layered testing device to quantitatively determine the concentration of a substance. The device consists of approximately four layers: a first porous layer impregnated with reagent system, adjacent to the first layer is a membrane having a plurality of regions with different permeabilities to the fluid being tested, adjacent to the second layer is a porous transmission layer followed by a display strip. Selective permeability here results from chemical reaction with the analyte or size selection due to pore size of membrane layer.

Literature describing a Millipore Immunozyme Toxoplasma Antibody Test, No. PB 847 (1979) discloses a cassette having a microporous immunosorbent, porous hydrophobic layer and an absorbent blotter. When the cassette top is depressed the liquid therein flows through the immunosorbent into the blotter. Thus, this device utilizes physical separation to prevent any background color which may form in the absorbent layer from interfering with the detection of results in the upper layer.

SUMMARY OF THE INVENTION

This invention relates to an improved assay device for detecting or quantitating the presence or absence of a substance in a sample suspected or known to contain said substance, said device having multiple layers comprising: (a) a permeable membrane having a capture reagent attached thereto, (b) an intermediate layer, and (c) an absorbent layer, wherein layer (b) is in direct communication with layers (a) and (c), the improvement wherein layer (b) is a selectively permeable membrane and has at least one hole therethrough, the hole is directly below the capture reagent, and the area of said hole or the combined area of a plurality of holes is less than the area covered by the capture reagent.

The assay devices of this invention can be utilized in immunoassays for detecting or measuring substances which can be captured by a member of a binding pair.

The invention also concerns treatment of an absorbent layer of an assay device with an enzyme inhibitor to reduce background color when an enzyme detection system is used.

FIGURES

DETAILED DESCRIPTION OF THE INVENTION

Figure 2:
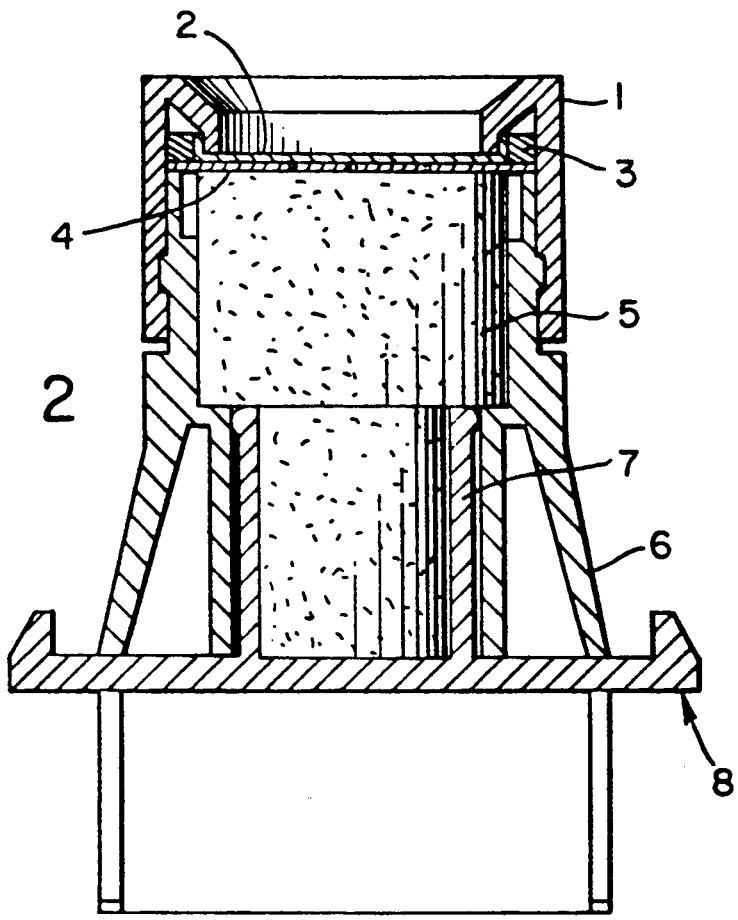
FIG. 2 is an elevational view in cross-section which illustrates the configuration of the device.

In this application, the term "selectively permeable" refers to materials which do not permit the substantial passage of aqueous solutions therethrough whether or not they permit the passage of other liquids such as organic solvents, if present.

According to the present invention, various types of receptor molecules can be used as the capture reagent, such as a member of any specific immune or non-immune binding pair as is discussed below. Selection of a suitable capture reagent will depend upon a variety of criteria, such as, the analyte of interest, the assay sensitivity needed in order to detect the analyte of interest, and the like. The preferred embodiment of this invention utilizes a monoclonal antibody or immunoreactive monoclonal antibody fragment as the capture reagent. However, if a monoclonal antibody having the appropriate affinity was not obtained, then a polyclonal antibody with the requisite affinity might be preferred in order to achieve the desired sensitivity.

In addition to the capture reagent, positive and negative control reagents can also be attached to the permeable layer surface to determine whether the assay and detection system are functioning properly.

Suitable positive control material can be purified antigen, if sample were added to the device without preincubation with detector antibody. It can be antigen bound to detector antibody, if a preincubation takes place with samples containing an analyte. This would demonstrate that captured complex of antigen and detector antibody can be detected in the assay, but not that such a complex could be formed or captured. If a biotin on the detector antibody is the key group tested, any material which has biotin attached could be substituted for the complex and serve as well for a positive control. Such materials include biotinylated bovine serum albumin or other biotinylated proteins. Another possible positive control material would be antibody to a component of the detection system, such as anti-enzyme. This would demonstrate that if the enzyme in the detection system is captured on the membrane, a positive result would occur. Other types of positive controls are possible. Thus, the selection of a suitable positive control is designed to test for a positive reaction if certain conditions are met (if antigen is present, or if biotin is present, or if enzyme is captured, etc.).

A good negative control material would be a monoclonal antibody of the same species and subclass as the capture antibody, applied at an equivalent concentration (quantity per unit area) to the capture antibody. The negative control antibody should have no demonstrable (in the assay) affinity for the antigen to be tested or for any component of the detection system. Thus, when properly utilized, the negative control provides a test for non-specific reactions.

Materials which can be used for the permeable layer, on which the capture reagent is spotted, include various natural or synthetic materials, which may be individual materials or combinations of materials, which may be organic, inorganic or combinations thereof. The permeable layer must be bibulous, i.e., it allows the flow of aqueous solutions therethrough without substantially impeding the movement of solutes employed in the assay. The material selected must also be one to which the capture reagent can be attached to a localized area of the device, either covalently or non-covalently, directly or indirectly as is discussed below. Exemplary materials which may find use are polysaccharides, e.g. cellulosic materials, such as paper, cellulose acetate, nitrocellulose, and backed nitrocellulose; inorganic materials, such as silica, deactivated alumina, diatomaceous earth, $MgSO_4$ or other inorganic finely divided material substantially uniformly dispersed in a porous polymer matrix, with polymers such as vinyl chloride, vinyl chloride-propylene copolymer, and vinyl chloride-vinyl acetate copolymer; cloth, both naturally occurring, e.g., cotton and synthetic, e.g. nylon cloth; porous gels, e.g. silica gel, agarose, dextran, and gelatin; polymeric films, e.g. polyacrylamide or the like.

There can also be mentioned, in particular, membranes to which proteins can be covalently attached.

The list includes the following which can be purchased commercially: microporous affinity membranes with a pore size in the range of about 0.5 to about 5 micrometers, membranes with a chemically preactivated surface which offer a high density of covalent binding sites that immobilize proteins on contact, and chemically activated hydrophilic microporous membranes wherein the base membrane is hydrophilic polyvinylidene fluoride, chemically derivatized to allow protein immobilization through epsilon amino groups of lysine or arginine in the pH range of 7 to 9. For a sensitive assay, the choice of membrane depends primarily upon the ability to prevent nonspecific binding on the membrane by blocking it. This in turn depends upon the reagents selected, the blocking agent, and the membrane itself. The preferred membrane in practicing the invention is a chemically activated hydrophilic microporous membrane.

The selectively permeable layer of this multi-layer device prevents the flow of aqueous solutions under the assay conditions. This resistance to flow is important because it increases the amount of time the capture reagent contacts the other reagents used in the assay, thus improving subsequent steps in building the sandwich and assaying the enzyme, as well as the overall sensitivity of the assay. A wide variety of compositions of known flow characteristics can be used for the selectively permeable layer which includes polyethylene, polyethylene-backed polytetrafluoroethylene and fibrous-porous polytetrafluoroethylene. A fibrous-pourous polytetrafluoroethylene membrane is the preferred material for the selectively permeable layer in practicing the instant invention. The fibrous-porous nature of the membrane appears to encourage radial flow along the surface so that liquid flows to the center where the holes are located in the selectively permeable layer. During the assay, no aqueous reagents pass through the pores in the fibrous-porous polytetrafluoroethylene membrane, which is selectively permeable with respect to the aqueous assay reagents.

Fibrous-porous polytetrafluoroethylene membranes are available in a variety of pore sizes ranging from about 1 to about 60 micrometers and a variety of thicknesses ranging from about 0.063 mm to about 0.65 mm. Due to the method of manufacture, these membranes reproduce the structure of standard filter papers down to the original fiber dimensions and arrangements.

In practicing the invention, it is preferred that fibrous-porous polytetrafluoroethylene or other selectively permeable membranes have a thickness in the range of about 0.1 mm to about 0.15 mm and a pore size of about 5 micrometers to about 6 micrometers. A membrane having a thickness of greater than about 0.15 mm is preferably avoided because this can interfere with the smooth flow of liquid through the holes. On the other hand, if the selectively permeable membrane is too thin then it will break when the device is being assembled. Also, thinner membranes tend to be more translucent and, thus, allow color which develops in the absorbent layer located beneath the selectively permeable membrane to show through the intermediate membrane. Transmission of color through the intermediate layer increases the difficulty of discriminating between low positive results and negative results.

The absorbent layer serves as a repository for excess reagent solutions. Consequently, all the reactants needed to produce color are present in the absorbent layer. Since development of color in the absorbent layer is not desirable, a variety of reagents can be added to the absorbent layer to reduce production of background color in the absorbent layer. According to the present invention, surprisingly and unexpectedly it has been found that when an enzyme-based detection system is used, color development in the absorbent layer can be minimized by saturation with a solution containing an enzyme inhibitor specific for the enzyme selected to detect.

Alkaline phosphatase is an enzyme which hydrolyzes many different esters of phosphoric acid and which has a relatively broad specificity, capable of acting on a number of different structurally related substrates, but at widely different rates. It is used quite frequently as part of a detection system in a wide variety of assay formats. A number of inhibitors are known for alkaline phosphatase. $Be^{++}$ and $Zn^{++}$ inhibit alkaline phosphatase. Inorganic phosphate which is a product of the reaction catalyzed by alkaline phosphatase is also an important inhibitor of the reaction. Many amino acids, including cysteine, histidine and phenylalanine are weak inhibitors of alakaline phosphatase. Chelating agents, such as EDTA (ethylenediaminetetraacetic acid) are inhibitors, probably because they remove essential $Zn^{++}$ ions from the structure of the enzyme (alkaline phosphatase is a zinc metalloprotein and requires structural zinc for activity, but excess zinc ions inhibit the enzyme as noted above). Iodosobenzoate, iodoacetamide, and 1,3,4,6-tetrachloro-3 alpha-6 alpha-diphenylglycouril also inhibit alkaline phosphatase.

Horseradish peroxidase (HRP) and beta-galactosidase are other enzymes commonly used for detection in various assay formats. HRP is inhibited by azide, fluoride, hydroxylamine, hydromethylhydrogen peroxide and reducing agents. Beta-galactosidase is inhibited by heavy metals, organomercuric compounds, metal chelating agents, alcohols and high concentrations of alkali ions including sodium ions.

Notwithstanding the multitude of publications that have been written about enzyme inhibition, none of these publications addresses the use of enzyme inhibitors to reduce background color development in the absorbent layer of an assay device using an enzyme detection system. Since enzyme detection is the preferred method of detection as discussed below and since reduction of background color development facilitates discrimination between weak positive results and negative results, enzyme inhibition, surprisingly and unexpectedly, was the best tool to regulate background color development in the absorbent layer.

It should be clear that many variations of the example discussed below are possible depending on factors such as the assay device used, detector enzyme selected, inhibitor chosen which is specific for the enzyme selected and solubility characteristics of the inhibitor. These variations fall within the scope of the invention.

The following illustrates how the absorbent layer of the device of this invention was treated in order to minimize background color production.

The absorbent layer was saturated with an isopropanol solution having about 200 mM zinc chloride and 0.3% of a surfactant such as an alkylarylpolyetheralcohol. For example, TRITON X-100 is an alkylarylpolyetheralcohol (polyethylene glycol p-isooctylphenyl ether). The surfactant made the layer hydrophilic and excess zinc ions prevented development of color in the absorbent layer by inhibiting the detector enzyme which, for this example, was alkaline phosphatase. Any surfactant known to those skilled in the art can be used to render the absorbent layer hydrophilic. Alkylarylpolyetheralcohol is merely one of many surfactants that would be appropriate.

Similarly, selection of a solvent in which to dissolve the inhibitor is not critical. Two considerations enter the selection of a suitable solvent: (1) what is the solubility limit of the inhibitor in the solvent; and (2) how quickly will the absorbent layer dry after being saturated with this solvent.

It was not necessary to immobilize zinc ions on the surface of the absorbent layer because the excess absorbing capacity of the absorbent layer prevented zinc ions or any reagents from migrating from the absorbent layer to any other layer. Thus, zinc ions remained within the absorbent layer to inhibit the alkaline phosphatase and did not interfere with color development on the surface of the permeable layer. Depending on the structure of the assay device, the inhibitor selected and the capacity of the absorbent layer, it might be desirable to immobilize the inhibitor on the absorbent layer.

Solid zinc chloride can be dissolved directly in isopropanol containing 0.3% of a surfactant alkylarylpolyetheralcohol, methanol, chloroform, or any other solvents satisfying the criteria mentioned above. It was also possible to use a 50% aqueous zinc chloride solution which can be purchased from Mineral Research, Inc. (Harrisburg, N.C.), to make the solution with which to saturate the absorbent layer.

When 50% aqueous zinc chloride solution was used, it was weighed so that about 206 grams of solution was dissolved per gallon of isopropanol containing 0.3% of an alkylarylpolyetheralcohol to achieve a final concentration of 200 mM zinc chloride in the isopropanol solution. Another approach was to saturate the absorbent layer with the isopropanol solution containing detergent, dry the layer and then saturate the absorbent layer with zinc chloride solution.

Selection of material suitable for the absorbent layer or layers is not critical. These materials include cellulose, cellulose acetate, polyester, porous polyethylene and other polyolefins such as polyethyleneterephthalate. What is important is that saturating the absorbent layer with an appropriate inhibitor solution minimizes development of background color so that virtually no color is transmitted through the selectively permeable layer.

Figure 1:
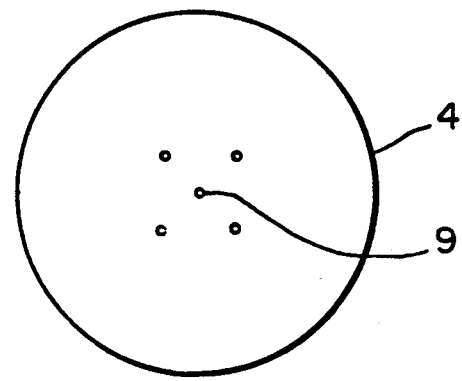
FIG. 1 illustrates a plan view of layer (b) having holes in accordance with the invention.

An essential feature of the selectively permeable layer is that it has from one to about seven holes extending through it which are directly below the capture reagent spotted on the permeable membrane and the size of the hole or holes covers an area less than that covered by the capture reagent. The preferred embodiment of this invention has five holes in the selectively permeable layer. One hole is in the center and the remaining holes are arranged symmetrically around the center hole as illustrated in FIG. 1. Other types of arrangements are also possible so long as they permit clear delineation of the circular capture reagent spot which defines a positive result at the end of the assay.

While the shape of the hole is not important, hole size is important. The holes can be circular, elliptical, rectangular, etc., but if the holes are too large, then flow control is lost. If a single hole is used which exceeds the diameter of the capture antibody spot, sensitivity is lost. Larger holes also tend to show through the top membrane as darker circles instead of dots, which could lead to confusion with weak positive results. These holes can have a size of about 25 micrometers by about 1000 micrometers. The preferred embodiment of this invention uses a selectively permeable layer having five holes arranged as discussed above. The preferred hole size is about 100 micrometers by about 300 micrometers. Holes of this size are obtained by using a 30 gauge needle. It is estimated that five holes having these dimensions occupy about 0.4% to 10% of the area under the capture antibody spot and when compared to the area of the upper surface of the permeable layer, this constitutes about 0.04% to about 1% of the entire upper surface of the permeable layer.

A device containing the foregoing layers is illustrated in FIG. 2. It has a cap 1, permeable layer 2, an O-ring 3, selectively permeable layer 4 having holes 9 as discussed above, absorbent plug 5 which fits into the body 6 which in turn rests on a base 7 having tabs 8. When the device has been assembled, the permeable layer 2, selectively permeable layer 4, and absorbent plug 5, are directly underneath each other because the O-ring 3 is forced into the cap. When tabs 8 are pulled down, a small vacuum is generated. This ensures that the reagents begin flowing properly through the device. Subsequent flow occurs without difficulty by capillary action.

Commonly used laboratory techniques, such as centrifugation, filtration, or a combination thereof, can remove particulate material from specimens before the assay. Some sample processing step may be necessary for some specimens which contain particulate material of dimensions larger than the pore size of the permeable layer. Particulate material of such a size will be trapped on the surface of the permeable layer, where it can cause background staining and thus interfere with assay performance.

Substances which can be detected and/or quantitated using the instant invention can be illustrated by the following: polypeptides and proteins, polysaccharides, nucleic acids, and combinations thereof, bacteria, viruses, chromosomes, genes, mitochondria, nuclei, cell membranes and the like. Exemplary proteins are nucleoproteins, glycoproteins, scleroproteins, proteoglycans, mucoproteins, histones, albumins, insulin, pepsin and the like. Furthermore, there can also be mentioned blood clotting factors such as fibrinogen, thrombin, etc., as well as, peptide and protein hormones such as glucagon, follicle-stimulating hormone, luteinizing hormone, etc. With respect to viruses, there can be mentioned the following: adenoviruses, herpes viruses such as herpes simplex, varicella zoster, herpes virus B, cytomegalovirus, Epstein-Barr virus, human herpes virus type 6; pox viruses; picornaviruses; orthomyxoviruses, paramyxoviruses; coronaviruses; rhabdoviruses; togaviruses; bunyaviruses; arenaviruses; rubella virus; arboviruses; reoviruses; hepatitis; retroviruses; oncogenic viruses and the like.

Although it was mentioned above that polyclonal antibodies can be used for the capture reagent, a preferred embodiment of this invention, as is mentioned above, utilizes a monoclonal antibody for the capture reagent. A monoclonal antibody is also preferably used for the detector reagent. Techniques for preparing the monoclonal antibodies of the present invention are well known and have been cited in a wide variety of publications, the following of which are incorporated by reference: Kohler and Milstein, Nature, 256:495–497 (1975), Pereira, et al., Infection and Immunity, Vol. 29, No. 2, pp. 724–732 (Aug. 1980), Oi et al., Immunoglobulin producing hybrid cell lines, pp. 351–371 in B. Mishell and S. Schiigi (ed.), Selected methods in cellular immunology, W. H. Freeman Co., San Francisco (1980) and Galfre et al., Preparation of Monoclonal Antibodies: Strategies and Procedures, Methods in Enzymology 73, pp. 1-46 (1981). These techniques will not be further described herein. Depending upon the sensitivity of the particular reagents for use in the assay, the best capture antibody may be either polyclonal or monoclonal.

Attachment to the permeable membrane, whether direct or indirect, covalent or non-covalent, can be achieved using well-known techniques. In a preferred embodiment, the capture reagent is attached covalently to the permeable membrane to avoid losing any reagents due to washing or as subsequent reagents are added.

In accordance with the invention the monoclonal antibody used for detection is labeled using conventional techniques. A component of a reporter system or a member of a specific binding pair may be used as the label.

Specific binding pairs may be of the immune or non-immune type. Immune specific binding pairs are exemplified by antigen-antibody systems or hapten/anti-hapten systems. There can be mentioned fluorescein-/anti-fluorescein, dinitrophenyl/anti-dinitrophenyl, biotin/anti-biotin, peptide/anti-peptide and the like. The antibody member of the specific binding pair may be produced by customary methods familiar to those skilled in the art. Such methods involve immunizing an animal with the antigen member of the specific binding pair, or with a portion of an antigen which can be synthetic or genetically engineered, such as a synthetic peptide. If the antigen member of the specific binding pair is not immunogenic, i.e. a hapten, it can be covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin B12, folic acid-folate binding protein and the like.

A variety of methods are available to covalently label monoclonal antibodies with a member of a specific binding pair. Methods are selected based upon the nature of the member of the specific binding pair, the type of linkage desired, and the tolerance of the antibody to various conjugation chemistries. For example, biotin can be covalently coupled to monoclonal antibodies by utilizing commercially available active derivatives. Some of these are biotin-N-hydroxysuccinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. If fluorescein is used, then it can be coupled to protein amine groups using fluorescein isothiocyanate. If dinitrophenyl groups are used, they can then be coupled to protein amine groups using 2,4-dinitrobenzene sulfonate or 2,4-dinitro-fluorobenzene. Other standard conjugation methods available to couple monoclonal antibodies to a member of a specific binding pair include dialdehyde coupling, carbodiimide coupling, homobifunctional crosslinking, and heterobifunctional crosslinking. Carbodiimide coupling is an effective method of coupling carboxyl groups on one substance to amine groups on another. Carbodiimide coupling is facilitated by using the commercially available reagent, 1-ethyl-3-(3-dimethyl-aminopropyl)carbodiimide (EDAC).

Homobifunctional crosslinkers, including the bifunctional imidoesters, are commercially available and are employed for coupling amine groups on one substance to amine groups on another. Heterobifunctional crosslinkers are reagents which possess two different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups may be a photoactive aryl nitrene, which upon irradiation reacts with a variety of groups. The preferred mode according to this invention is conjugating monoclonal antibodies with biotin via an N-hydroxysuccinimide ester.

In order to facilitate signal detection, either the monoclonal antibody or a member of a specific binding pair is labeled with a component of a reporting system. The term reporting system refers to the reporter selected and any means of linking the reporter to the monoclonal antibody or to a component of a specific binding pair. Thus, a reporter can be linked directly or indirectly, covalently or non-covalently to a monoclonal antibody or to a member of a specific binding pair. Reporters may be radioactive isotopes, enzymes, fluorogenic, magnetic, chemiluminescent or electrochemical materials. Two commonly used radioisotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$.

Enzymes are also used as reporters for immunoassays. These include horseradish peroxidase, alkaline phosphatase, Beta-galactosidase, glucose oxidase, luciferease, Beta-lactamase, urease and lysozyme. Labeling with enzymes is facilitated by using dialdehyde, carbodiimide coupling, homobifunctional crosslinkers as described above for labeling monoclonal antibodies with members of specific binding pairs. The labeling method chosen depends on the functional groups available on the enzyme and the material to be labeled, and the tolerance of both to the conjugation conditions. The labeling method used in the present invention can be one of any conventional methods currently employed, including those described by Engvall and Pearlmann, Immunochemistry 8, 871 (1971), Avrameas and Ternynck, Immunochemistry 8, 1175 (1971), Ishikawa et al., J. Immunoassay 4(3):209-327 (1983) and Jablonski, Anal. Biochem. 148:199 (1985). Labeling can be accomplished by indirect methods such as using spacers or other members of specific binding pairs. An example of this is the detection of biotinylated antibodies with unlabeled streptavidin and biotinylated enzyme, with the unlabeled streptavidin and biotinylated enzyme being added either sequentially or simultaneously. Detection of enzyme activity can be facilitated by measuring chromogenic, fluorogenic, magnetic, chemiluminescent or electrochemical changes by commonly known methods.

Reporters can be fluorogenic, magnetic, or chemiluminescent in nature. In addition, reporters may be detectable by electrochemical means. Some methods of labeling with these reporters are described above. In a preferred embodiment, the enzyme, alkaline-phosphatase is used as the reporter and 5-bromo-4-chloroindoxyl phosphate (hereinafter BCIP) and 2,2'-di-(p- nitrophenyl)-5,5'-diphenyl-3,3'-(3,3'-dimethoxy-4,-4'-diphenylene) -ditetrazolium chloride (hereinafter NBT) are used for the substrate.

The monoclonal antibodies useful in the present invention can be of the IgG type as well as other immunoglobulin classes.

Moreover, these monoclonals can be directed to a multitude of antigenic determinants depending upon the target. By way of illustration only, there can be mentioned antigenic determinants associated with nucleocapsid proteins, glycoproteins or viral envelopes.

In a preferred embodiment for virus detection, this invention also employs a collection and transport system specifically for the transport of samples for testing by immunoassay according to the invention.

The collection system utilizes any appropriate means of collecting a virus and the transport system utilizes a tube containing buffered surfactant solution. After sample collection, the specimen is immersed in the buffered surfactant. Direct immersion lyses the virus in the sample thus making more antigen accessible for testing and stabilizes the antigen during transport. The solution also contains a carrier protein which minimizes nonimmunologic binding of the proteins in the sample, either to each other or to surfaces with which they come in contact.

The following surfactants can be mentioned as falling within the scope of the invention and should not be construed as limiting: non-ionic surfactants such as polyoxyethylene ethers and alkylphenoxypolyethoxy compounds; ionic surfactants such as alkyl/aryl sulfonates/sulfates; zwitterionic surfactants; bile salts and derivatives thereof such as octyl glucopyranoside and dodecyl maltoside.

Exemplary carrier proteins include serum, albumin, gelatin and casein.

Any buffer compatible with the assay system can be used to practice the invention.

In a most preferred embodiment, the buffer is phosphate buffered saline, the surfactant is NONIDET P-40 (NP40) which is an alkyl phenol-ethylene oxide condensate, and the carrier protein is bovine serum albumin.

The following example is intended to illustrate the invention and should not be construed as a limitation thereon.

EXAMPLE 1

Monoclonal Antibody Preparation

The capture monoclonal antibody identified as 55307 and the detector monoclonal antibody identified as 55306 were prepared according to the methods of L. Pereira, et al., as described in Infection and Immunity, Vol. 29, No. 2, pp. 724–732 (Aug. 1980) and Oi et al. as described in Immunoglobulin Producing Hybrid Cell Lines, pp. 351–371, in B. Mishell and S. Schiigi (ed.), Selected Methods in Cellular Immunology, W. H. Freeman Co., San Francisco.

55306 and 55307 both react with glycoprotein gD from either HSV-1 or HSV-2. Epitope specificities were determined by competing an unlabeled antibody with a biotin labeled antibody for solid phase antigen. When an unlabeled antibody did not inhibit the binding of a labeled antibody, it was determined that the antibodies were directed against different epitopes. Antibodies 55306 and 55307 were found to have specificity for different epitopes on HSV 1 and 2 antigen gD.

Monoclonal antibodies were purified from ascites fluid by salt fractionation with 40% saturated ammonium sulfate and gel filtration on SEPHACRYL S-300 (Pharmacia, Inc., Piscataway, N.J., a pourous polyacrylamide). Monoclonal antibody 55306 was biotinylated as described below.

Antibody Biotinylation

A solution of antibody 55306 was dialyzed against 0.1M $NaHCO_3$ buffer, pH 8.4, and adjusted to a concentration of 1 mg in 1 ml. A 50 fold molar excess of a biotin-N-hydroxysuccinimide ester (commercially available from a variety of sources including Sigma Chemical Co. (St. Louis, Mo.) and Calbiochem (San Diego, Calif.)) in 0.1 ml dimethylsulfoxide was added and allowed to react for 2 hours at room temperature, at which time 0.1 ml of 2M Tris(hydroxymethyl)aminomethane (hereinafter referred to as Tris-HCl buffer) pH 8.0 was added. After 15 minutes, 1 ml of 1% bovine serum albumin (Sigma) in phosphate buffered saline (PBS), pH 7.4 was added and the solution dialyzed against PBS. The biotinylated antibody was stored at 4° C.

Assay Reagents, Materials and Device

Assay Materials

Chemically activated membranes (Cat. No. IASD00005), as described above, were purchased from Millipore Corporation (Bedford, Mass.) for use as the permeable layer.

Zinc chloride treated absorbent plugs having the configuration 5 illustrated in FIG. 2 were manufactured by Pore Technology Limited (Somerville, Mass.) as follows: porous polyethylene plugs were saturated with isopropanol having 200 mM zinc chloride and 0.3% TRITON X-100. 50% aqueous zinc chloride was purchased from Mineral Research, Inc. (Harrisburg, N.C.). 206 grams of the aqueous zinc chloride was dissolved per gallon of isopropanol containing 0.3% TRITON X-100. Plugs were saturated in the enzyme-inhibitor containing solution and then removed and allowed to dry before using.

10-fold concentrated PBS (Cat. No. 310-4200) was purchased from GIBCO (Grand Island, N.Y.) and was diluted 1/10 with distilled water.

HIPURE Liquid Gelat'n (45% w/v) was obtained from Norland Products, Inc. (695 Joyce Kilmer Avenue, New Brunswick, N.J.), and is hereinafter referred to as gelatin.

Streptavidin and alkaline phosphatase were purchased from Scripps Laboratories (San Diego, Calif.) and were conjugated using the one step glutaraldehyde method as described by E. Engvall and P. Perlmann, Immunochemistry 8, 871 (1971) which is hereby incorporated by reference.

The substrate for the enzyme assay was BCIP/NBT in a Tris-HCl buffer. These reagents are commercially available from companies such as Kirkegaard and Perry, Gaithersburg, Md.

The capture and detector monoclonal antibodies were prepared, purified and as discussed above and the detector antibody was biotinylated as discussed above.

The standard antigen preparation was UT 0329841 HSV-1. The negative antigen was UT 041185. Both were purchased from Viral Antigens, Inc. (Memphis, Tenn.).

The standard antigen preparation and the negative control were diluted in the sample diluent as discussed below.

Assay Solutions

PBS was purchased as a 10-fold concentrate and diluted 1/10 with distilled water as mentioned above.

Standard antigen diluent was PBS containing 0.50% bovine serum albumin (BSA), 0.7% NONIDET P-40, and 0.1% azide, pH 7.4. The solution was filtered through a 0.22 micrometer pore size membrane.

The detector antibody diluent was 0.2M Hepes buffer containing 4% heated normal rabbit serum (GIBCO), 0.85% NaCl and 0.1% azide, pH 7.5. Before use, the solution was heated overnight at 50° C. and filtered through a 0.22 micrometer pore size filter.

Conjugate diluent was PBS containing 1% BSA, 0.05% TWEEN 20 which is a polyoxyethylene sorbitan mono-oleate, and 0.1% azide, pH 7.4. The solution was filtered through a 0.22 micron membrane.

Substrate buffer was purchased from Kirkegaard and Perry. The solution was filtered through a 0.22 micron membrane.

Wash buffer was Substrate buffer to which was added 0.05% TWEEN 20.

Stop solution was 1.0N HCl.

Biotinylated detector antibody identified as 55306 above was diluted 1/40 in the Detector antibody diluent discussed above. The standard antigen preparation and the negative antigen preparation were diluted with standard antigen diluent as discussed above. The streptavidin-alkaline phosphatase conjugate was diluted 1/500 in Conjugate diluent and the substrate was prepared just prior to use by adding 1 ml of BCIP and 1 ml of NBT to 10 ml of Substrate Buffer.

Device Preparation

The permeable membrane was spotted with 2 microliters of the capture monoclonal antibody identified as 55307 above. The capture reagent was diluted to a concentration of 2 mg/ml before spotting.

After the membrane had dried for about 5 to 30 minutes, it was blocked overnight with 5% gelatin in PBS at about 37° C. in a humidified chamber. The blocking solution was carefully aspirated through the membrane and the membrane was allowed to dry before use.

Five holes of about 100 by about 300 micrometers, in an area under the capture antibody spot having a diameter of about 3-4 millimeters, were made in the fibrous-porous polytetrafluoroethylene membrane. Best results were obtained using a 30 gauge needle to make five holes in an area under the capture antibody spot. A symmetrical arrangement worked best wherein four holes were arranged symmetrically around the fifth hole in the center.

The device was assembled as discussed above.

Assay Protocol 0.2 ml of antigen was mixed with 0.2 ml of detector antibody diluted in detector antibody diluent in a polyethylene tube and incubated for 1-10 minutes at room temperature to allow the antigen to react with the biotinylated detector antibody. It should be noted that when a sample, other than the standard antigen, is assayed, then the sample may require removal of particulate matter as discussed above.

After incubation, the mixture was added to the assay device. The tabs were pushed down to assure that good reagent flow through the holes was started. The sample liquid was absorbed by the device in about 5 minutes. Incubation was continued for another 5 minutes (10 minutes from sample addition) at room temperature to allow the antigen-biotinylated antibody to bind to the capture antibody. This was followed by the addition of 0.2 ml of conjugate which was incubated for 10 minutes at room temperature to allow the streptavidin-alkaline phosphatase conjugate to bind to the biotinylated detector antibody. This was followed by the addition of 0.4 ml of wash buffer. When the wash buffer was fully absorbed, 0.2 ml of substrate was added to the device, followed by incubation at room temperature to allow color to develop. After 10 minutes, an additional 0.2 ml of substrate was added. After 10 minutes, 0.2 ml of stop solution was added.

The membrane can be removed, washed with water and allowed to dry before storing to record results. Dry membranes are stable for a few months if protected from light.

What is claimed is:

1. In a membrane-based assay device for detecting or quantitating the presence or absence of a substance in a sample suspected to contain said substance, said device having multiple layers comprising:
   (a) a permeable membrane having attached thereto a capture reagent which specifically binds to said substance.
   (b) an intermediate layer, and
   (c) an absorbent layer,
   wherein layer (b) is in direct communication with layers (a) and (c),
   the improvement wherein layer (b) is a substantially water impermeable membrane, the membrane having at least one hold therethrough, the hole or holes are directly below the capture reagent and the area of the hole or the combined areas of the holes is less than the area covered by the capture reagent and the improvement further wherein the absorbent layer is saturated with an enzyme inhibitor-containing solution to reduce background color development.

2. The device according to claim 1 wherein layer (b) has from about one to about seven holes.

3. The device according to claim 1 wherein the capture reagent is attached covalently.

4. The device according to claim 2 wherein said hole or holes are about 25 micrometers by about 1000 micrometers.

5. The device according to claim 2 wherein said hole or holes occupy 0.4% to about 10% of the area under the capture reagent.

6. The device according to claim 1 wherein the capture reagent is a monoclonal antibody or an immunoreactive monoclonal antibody fragment.

7. The device according to claim 1 wherein layer (a) is selected from the group consisting of microporous affinity membranes, membranes with a chemically preactivated surface, and chemically activated hydrophilic microporous membranes.

8. The device according to claim 1 wherein layer (b) is a fibrous-pourous polytetrafluoroethylene membrane.

9. The device according to claim 1 wherein the capture reagent is a member of an immune binding pair.

10. The device according to claim 1 wherein the absorbent layer is saturated with a zinc chloride solution.

11. A membrane-based immunoassay for detecting or quantitating the presence or absence of a substance in a sample suspected to contain said substance which is performed in a membrane-based immunoassay device having multiple layers comprising:
(a) a permeable membrane having a capture reagent attached thereto,
(b) an intermediate layer, and
(c) an absorbent layer, wherein layer (b) is in direct communication with layer (a) and (c),
wherein the sample, detector reagent and other reagents used in the immunoassay are added to the layer (a) and the substance bound to capture reagent on layer (a) is detected or quantitated;
the improvement wherein layer (b) is a substantially water impermeable membrane, the membrane having at least one hole therethrough, the hole or holes are directly below the capture reagent and the area of the hole or the combined areas of the holes is less than the area covered by the capture reagent and the improvement further wherein the absorbent layer is saturated with an enzyme inhibitor-containing solution to reduce background color development.

12. The immunoassay according to claim 11 wherein the substance to be detected or quantitated is selected from the group consisting of polypeptides, proteins, polysaccharides, nuclei acids, blood clotting factors, hormones, bacteria and viruses.

13. The immunoassay according to claim 12 wherein the substance to be detected is a virus selected from the group consisting of adenoviruses, herpes simplex, varicella zoster, herpes virus B, cytomegalovirus, Epstein-Barr virus, pox virus, picornaviruses, orthomyxoviruses, paramyxoviruses, coronaviruses, rhabdoviruses, togaviruses, bunyaviruses, arenaviruses, rubella virus, arboviruses, reoviruses, hepatitis, retroviruses and oncogenic viruses.

14. The immunoassay according to claim 13 wherein the sample is transferred directly into a viral transport tube containing a buffered detergent solution comprising buffer, detergent and a carrier protein which minimizes nonimmunologic binding of proteins in the sample.

15. The immunoassay according to claim 11 wherein the capture reagent is a monoclonal antibody or an immunoreactive monoclonal antibody fragment.

16. The immunoassay according to claim 11 wherein the capture reagent is a member of an immune binding pair.

17. The immunoassay according to claim 11 wherein the detector reagent is selected from a member of an immune binding pair.

18. The immunoassay according to claim 11 wherein the detect reagent is a monoclonal antibody or immunoreactive monoclonal antibody fragment.

19. The immunoassay according to claim 18 wherein the antibody or fragment may be labeled or unlabeled and when the antibody or fragment is unlabeled then it is reacted with a labeled antibody to the unlabeled antibody or fragment.

20. The immunoassay according to claim 18 wherein the antibody or fragment is labeled with a component of a reporter system or is labeled with a first member of a specific immune or non-immune binding pair.

21. The immunoassay according to claim 20 wherein the monoclonal antibody or fragment is labeled with a reporter selected from the group consisting of radioactive isotopes, enzymes, fluorogenic, magnetic, chemiluminescent and electrochemical materials.

22. The immunoassay according to claim 20 wherein the antibody or fragment is reacted with the second member of the binding pair to which is attached a reporter selected from the group consisting of radioactive isotopes, enzymes, fluorogenic, magnetic, chemiluminescent and electrochemical materials.

23. The immunoassay according to claim 18 wherein the antibody or fragment is labeled with biotin.

24. The immunoassay according to claim 23 wherein the biotinylated antibody or fragment is reacted with streptavidin-alkaline phosphatase.

25. The immunoassay according to claim 24 wherein the product of claim 21 is reacted with 5-bromo-4-chloro-indoxyl phosphate (BCIP) and 2,2'-di-(p-nitrophenyl) -5,5'-diphenyl-3,3'-(3,3'-dimethoxy-4,4'-diphenylene) -ditetrazolium chloride (NBT) as enzyme substrate.

* * * * *